United States Patent
Akiyama et al.

(10) Patent No.: US 11,371,982 B2
(45) Date of Patent: Jun. 28, 2022

(54) METHOD OF PREDICTING PATIENT PROGNOSIS USING RARE CELLS

(71) Applicants: TOSOH CORPORATION, Yamaguchi (JP); TOKYO METROPOLITAN GOVERNMENT, Tokyo (JP)

(72) Inventors: Yasuyuki Akiyama, Kanagawa (JP); Atsushi Morimoto, Kanagawa (JP); Toru Futami, Kanagawa (JP); Fumiaki Koizumi, Tokyo (JP); Takeshi Sawada, Tokyo (JP)

(73) Assignees: TOSOH CORPORATION, Yamaguchi (JP); TOKYO METROPOLITAN GOVERNMENT, Tokyo (JP)

( * ) Notice: Subject to any disclaimer, the term of this patent is extended or adjusted under 35 U.S.C. 154(b) by 85 days.

(21) Appl. No.: 16/070,706

(22) PCT Filed: Jan. 19, 2017

(86) PCT No.: PCT/JP2017/001817
§ 371 (c)(1),
(2) Date: Jul. 17, 2018

(87) PCT Pub. No.: WO2017/126634
PCT Pub. Date: Jul. 27, 2017

(65) Prior Publication Data
US 2019/0025282 A1   Jan. 24, 2019

(30) Foreign Application Priority Data
Jan. 19, 2016  (JP) .............................. JP2016-008259

(51) Int. Cl.
G01N 33/49    (2006.01)
G01N 33/574   (2006.01)
(Continued)

(52) U.S. Cl.
CPC ....... *G01N 33/491* (2013.01); *G01N 15/0205* (2013.01); *G01N 33/48* (2013.01);
(Continued)

(58) Field of Classification Search
CPC ................. G01N 33/491; G01N 33/48; G01N 33/57492; G01N 15/0205;
(Continued)

(56) References Cited

U.S. PATENT DOCUMENTS

2012/0276555 A1   11/2012   Kuhn et al.
2016/0223521 A1   8/2016    Okamoto et al.

FOREIGN PATENT DOCUMENTS

JP   2008-533487   8/2008
JP   2011-163830   8/2011
(Continued)

OTHER PUBLICATIONS

Millner et al. (Circulating Tumor Cells: A Review of Present Methods and the Need to Identify Heterogeneous Phenotypes, Annals of Clinical and Laboratory Science, 43, 3, 2013) (Year: 2013).*

(Continued)

*Primary Examiner* — Benjamin R Whatley
*Assistant Examiner* — Jean Caraballo-Leon
(74) *Attorney, Agent, or Firm* — Greenblum & Bernstein, P.L.C.

(57) ABSTRACT

The purpose of the present invention is to provide a method for accurately predicting a cancer patient prognosis based on a count of desired cells for which expression of a leukocyte marker and an epithelial marker is hardly exhibited by detecting those cells. Provided is a method for diagnosing an overall survival prognosis for a patient suffering from cancer, the method including: a step of obtaining a concentrated solution containing desired cells by pre-treating a biological
(Continued)

sample obtained from the patient; a step of optically detecting the concentrated cells; and a step of detecting the desired cells from the detected image, wherein an association is made with the overall survival prognosis diagnosis by counting the detected desired cells, and wherein the desired cells are cells confirmed by the existence of a cell nucleus and in which expression of a leukocyte marker and an epithelial marker is hardly exhibited.

17 Claims, 6 Drawing Sheets

(51) Int. Cl.
*G01N 33/50* (2006.01)
*G01N 33/487* (2006.01)
*G01N 15/02* (2006.01)
*G01N 33/48* (2006.01)
*G01N 15/10* (2006.01)
*G01N 15/00* (2006.01)
*G01N 15/06* (2006.01)
*G01N 15/14* (2006.01)

(52) U.S. Cl.
CPC ... *G01N 33/48735* (2013.01); *G01N 33/5002* (2013.01); *G01N 33/574* (2013.01); *G01N 33/57492* (2013.01); *G01N 2015/0019* (2013.01); *G01N 2015/0294* (2013.01); *G01N 2015/0693* (2013.01); *G01N 2015/1006* (2013.01); *G01N 2015/1081* (2013.01); *G01N 2015/1087* (2013.01); *G01N 2015/1486* (2013.01); *G01N 2333/4742* (2013.01); *G01N 2333/70589* (2013.01)

(58) Field of Classification Search
CPC ......... G01N 33/48735; G01N 33/5002; G01N 33/574; G01N 2333/70589; G01N 2015/1006; G01N 2333/4742; G01N 2015/0019; G01N 2015/0294; G01N 2015/0693; G01N 2015/1081; G01N 2015/1087; G01N 2015/1486
See application file for complete search history.

(56) References Cited

FOREIGN PATENT DOCUMENTS

| | | |
|---|---|---|
| JP | 2013-508729 | 3/2013 |
| JP | 2015-006169 | 1/2015 |
| WO | 2006/104474 | 5/2006 |
| WO | 2015/046557 | 4/2015 |
| WO | 2015/174539 | 11/2015 |

OTHER PUBLICATIONS

GE Healthcare (Isolation of Mononuclear Cells Methodology and Applications, GE Health Care Life Sciences, 2014). (Year: 2014).*
Boyum et al. (Separation of Leukocytes: Improved Cell Purity by Fine Adjustments of Gradient Medium Density and Osmolality, Scand. J. Immunology, 34, pp. 697-712, 1991). (Year: 1991).*
De Wit et al. (EpCAMhigh and EpCAMlow circulating tumor cells in metastatic prostrate and breast cancer patients, Oncotarget, 2018, 9, 86, pp. 35705-35716) (Year: 2018).*
Simon A. Joosse et al., "Cancer Research, 73", pp. 8-11.
International Search Report in International Patent Application No. PCT/JP2017/001817, dated Mar. 21, 2017.
International Preliminary Report on Patentability in International Patent Application No. PCT/JP2017/001817, dated Jul. 24, 2018.

* cited by examiner

METHOD OF PREDICTING PATIENT PROGNOSIS USING RARE CELLS

FIELD

The present invention relates to a method of predicting prognosis of a cancer patient with high accuracy by detecting cells in which leukocyte markers and epithelial markers are hardly exhibited (hereinafter referred to as "target cells") among rare cells present in a biological sample.

BACKGROUND

Diagnosis for clarifying prognosis of a cancer patient provides important information for therapeutic strategy or monitoring of therapeutic effects. Therefore, such diagnosis can be a useful benchmark for optimal therapy selection. Prognostic diagnosis provides a physician with information on the risk of pathological conditions of a patient and the probability of survival, thereby allowing the physician to select the optimal therapy, which leads to reduction of the risk of performing unnecessary treatment on the patient. Therefore, it is possible for prognostic diagnosis to not only save the cost of unnecessary treatment but also contribute to the improvement of the patient's prognosis by optimal treatment selection.

As auxiliary diagnosis for treatment, diagnosis is made using soluble tumor antigens. Since soluble tumor antigens are secreted from tumor cells, they can be detected in blood or tissue samples. Accordingly, there have been attempts to use soluble tumor antigens for many kinds of diagnoses such as monitoring of therapeutic effects. For example, CEA (Carcinoembryonic Antigen) and CA19-9 (Carbohydrate Antigen 19-9) are used as tumor markers of digestive organ cancers. However, since soluble tumor antigens are also released upon destruction of tumor cells, it is not always that they reflect prognosis of a cancer patient.

As cancer diagnosis markers that can replace soluble tumor antigens, circulating tumor cells (CTC) present in biological samples have been used. In Patent Literature 1 (JP2008-533487), cells are immunomagnetically concentrated for epithelial markers that are expressed on the CTC surface, and it is detected whether or not concentrated cells are CTCs based on immunofluorescent labeling of epithelial markers. According to Patent Literature 1, a method of providing prognosis indicators regarding disease progression and mortality by evaluating the absolute number of CTCs in a metastatic breast cancer patient and changes in such numbers has been realized.

It is reported in Non Patent literature 1 (Simon, A, Joosse. et al., CANCER RESEARCH, 73, 8-11 (2013)) that mesenchymal cells, which have experienced epithelial-mesenchymal transition, and in which expression levels of epithelial markers are low, are present in tumor tissues rich in epithelial cells, and such mesenchymal cells are involved in cancer metastasis. This report suggests that detection of CTCs alone in which expression levels of epithelial markers are high is not enough to accurately reflect the pathological state of a patient. However, there have been no reports on a method of predicting prognosis of a cancer patient based on the number of detected cancer-related cells in which epithelial markers are not expressed.

CITATION LIST

Patent Literature

Patent Literature 1: JP2008-533487

Non Patent Literature

Non Patent Literature 1: Simon, A. Joosse. et al., CANCER RESEARCH, 73, 8-11 (2013)

SUMMARY

Technical Problem

It is an object of the present invention to provide a method of predicting prognosis of a cancer patient with high accuracy by detecting and counting target cells in which leukocyte markers and epithelial markers are hardly exhibited.

Solution to Problem

The present inventors made intensive studies to achieve the above object and realized the present invention.

In other words, a first aspect of the present invention is:
a method of determining overall survival prognosis for a patient suffering from cancer, comprising steps of:
1) obtaining a concentrated liquid by concentrating target cells from a biological sample obtained from the patient;
2) optically detecting and counting cells contained in the concentrated liquid, the cells each having cell nucleus and not substantially expressing a leukocyte marker and an epithelial marker; and
3) associating the number of counted target cells and overall survival prognosis.

In addition, a second aspect of the present invention is a method according to the first aspect, characterized in that the target cells are cells having sizes larger than the sizes of erythrocytes and leukocytes. Further, a third aspect of the present invention is a method according to the first or second aspect, characterized in that the concentration step is a concentration method based on a specific gravity difference of a biological sample. Further, a fourth aspect of the present invention is the method according to any one of the first to third aspects, characterized in that the pretreatment includes concentrating a biological sample using a structure, in which one end is closed to form a bottom and the other end has an opening and which has a cap for sealing the opening, and wherein the structure is formed with at least two tubular members such that the structure is separable at a separation unit.

Advantageous Effects of Invention

The present invention relates to a method of predicting prognosis of a cancer patient with high accuracy by counting target cells, characterized by detecting desired cells in which CD45 and an epithelial marker are hardly exhibited. According to the method of the present invention, overall survival prognosis of a cancer patient can be determined by counting desired cells, which reflect the pathological state of the cancer patient, and in which epithelial markers are hardly exhibited.

DESCRIPTION OF EMBODIMENTS

The present invention relates to a method of determining overall survival prognosis for a patient suffering from cancer, comprising steps of:

1) obtaining a concentrated liquid by concentrating target cells from an organism sample obtained from the patient;

2) optically detecting and counting cells contained in the concentrated liquid, the cells each having cell nucleus and not substantially expressing a leukocyte marker and an epithelial marker; and 3) associating the number of counted target cells and overall survival prognosis.

In the present invention, overall survival prognosis is determined for the subject who is a patient suffering from cancer. A cancer from which the patient is suffering may be any cancer such as a primary cancer or a metastatic cancer. Examples of a cancer from which a patient is suffering include, but are not limited to, for example, cancers selected from the following group: hematopoietic malignant tumors such as leukemia, lymphoma, Hodgkin's disease, non-Hodgkin's lymphoma, and multiple myeloma; and brain tumor, breast cancer, endometrial cancer, cervical cancer, ovarian cancer, esophageal cancer, gastric cancer, appendiceal cancer, large bowel cancer, liver cancer, gallbladder cancer, bile duct cancer, pancreatic cancer, adrenal cancer, gastrointestinal stromal tumor, mesothelioma; larynx and oral cancers such as cancer of the floor of the mouth, gum cancer, tongue cancer, and buccal mucosa cancer; head and neck cancer, salivary gland carcinoma, paranasal sinus cancer, thyroid cancer, renal cancer, lung cancer, osteosarcoma, bone cancer, prostate cancer, testicular cancer, renal cancer, bladder cancer, skin cancer, and anal cancer. The patient may be a patient after receiving treatment, or may be a patient before receiving treatment, but the patient after receiving treatment is preferable from the viewpoint of determining therapeutic prognosis.

In the present invention, the term "organism sample" refers to any sample as long as it is a sample containing cells, including a biological sample obtained from a living body and a culture sample obtained via cell culture or tissue culture. Examples of a biological sample include samples from urine, blood, plasma, serum, saliva, semen, feces, sputum, cerebrospinal fluid, amniotic fluid, lymph fluid, ascites, cell aggregates, tumors, organs such as lymph nodes or arteries, and tissues of liver, lung, spleen, kidney, and skin. Examples of culture samples include cell cultures, tissue cultures, and culture solutions thereof. These organism samples can be prepared in advance in the form of liquid samples by performing a treatment such as dilution, mixing, dispersion, or suspension according to type of the sample.

An object of the present invention is to detect living cells of interest in an organism sample (hereinafter also referred to as "target cells"). Target cells detected in the present invention may be any cells depending on an experiment. For example, erythrocytes, leukocytes, stem cells represented by ES cells and iPS cells, endothelial cells, bacteria, and microorganisms and the like can be targeted. From the viewpoint of conducting early diagnosis and metastasis diagnosis of cancers, it is preferable to mainly target cancer cells. Among the cancer cells to be targeted in the present invention, it is preferable to target circulating tumor cells (CTCs) which distantly metastasize through the circulatory system of blood, lymph, or the like. Examples of such cancer cells include, for example, cells from gastric cancer, large bowel cancer, esophageal cancer, liver cancer, lung cancer, pancreatic cancer, bladder cancer, breast cancer, oral cancer (squamous cell carcinoma), uterine cancer (epithelial tumor), and blood cell cancer (lymphoma or leukemia). When CTC cells are target cells, the target cells are cells that have a nucleus and do not substantially express leukocyte markers and epithelial markers, The expression "not substantially express leukocyte markers and epithelial markers" means that expression of these markers is hardly exhibited. For example, as compared with marker expression control cells such as leukocytes that express leukocyte markers and epithelial cells that express epithelial markers, when the expression of the markers is less than half, preferably less than 1/3, more preferably less than 1/5, still more preferably less than 1/10, cells can be regarded as not substantially expressing such markers. Negative control cells that are known for not expressing leukocyte markers and epithelial markers, which are, for example, cells comparable to vascular endothelial cells or mesenchymal stem cells in terms of expression, can be determined to be cells that do not substantially express such markers.

Concentration Step

A concentration step is a step of concentrating target cells from an organism sample to obtain a concentrated liquid. By using specific gravity separation for separating and recovering a fraction containing target cells from a cell suspension, it is possible to increase the proportion of target cells relative to all cells. Using a container that can separate a cell suspension into a portion accommodating the fraction containing target cells and a portion accommodating a fraction containing foreign substances and/or non-target cells in the cell suspension makes it easy to separate and recover the fraction containing target cells by specific gravity separation. In general, specific gravity differs between living cells and dead cells, living cells can be separated from dead cells so as to be concentrated by utilizing the difference in specific gravity of the organism sample. In addition, since the specific gravity of damaged cells becomes high, intact cells among target cells can be separated, which is preferable (see WO2014/192919).

In such a concentration step, specifically, target cells can be concentrated using a density gradient solution. Among organism samples, for example, various cells such as erythrocytes, leukocytes, and platelets are present in a blood sample. In order to detect target cells in a later step, it is desirable to increase the proportion of target cells relative to all cells. It is possible to carry out the concentration step by overlaying an organism sample in a density gradient solution and centrifuging the solution. Thus, living target cells can be recovered from a zone formed in the density gradient solution, thereby making it possible to concentrate living target cells. A person skilled in the art can appropriately select a centrifugal speed and a density gradient so that concentration is achievable.

As described above, living cells can be separated and concentrated in the concentration step. Such a concentration step is not intended to completely separate living cells. It is enough to simply increase the proportion of living cells in the concentration step. The proportion of dead cells after the concentration step is less than 20%, preferably less than 15%, more preferably less than 10%, still more preferably less than 5%, although it may also vary depending on the mixing rate of dead cells in an organism sample.

Figure 1:
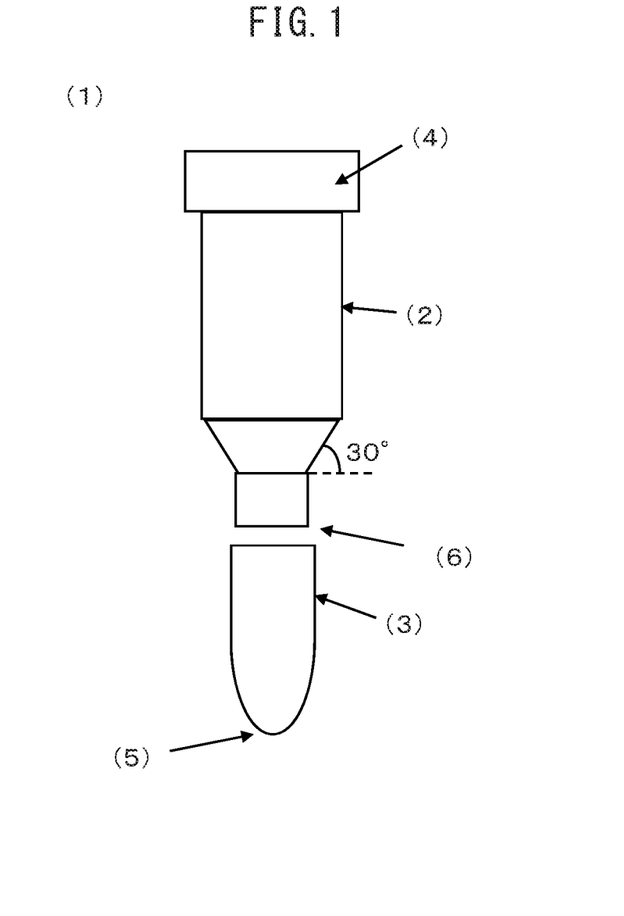
FIG. 1 is a view for explaining a separation and concentration structure used in the present invention.

As an instrument for performing the concentration step, for example, the cell separation and concentration structure of FIG. 1 can be used. The separation and concentration structure 1 is formed with two tubular members 2 and 3. The tubular member 2 constituting the upper portion of the separation and concentration structure has an opening, and the tubular member 3 has one closed end forming a bottom 5. The tubular members 2 and 3 have an opening and a communication opening 6 provided on the opposite end of the bottom, respectively, such that when the both members are connected, the internal spaces of both the tubular members become communicated with each other. Thus, the tubular members form a single separation and concentration structure as a whole.

Figure 5:
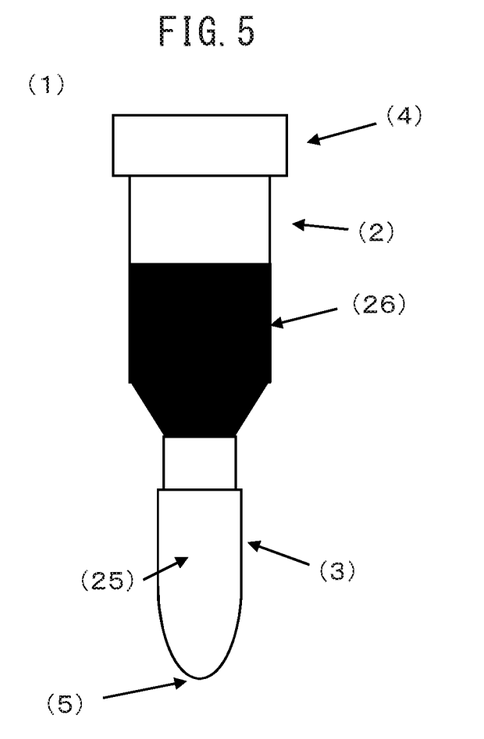
FIG. 5 is a view for explaining a method of concentrating target cells using the structure in FIG. 1

A density gradient solution 25 is injected into the separation and concentration structure 1 such that it fills from the bottom (a closed end 5 of the tubular member 3) to nearby the separation unit of the structure (FIG. 5). More specifically, it is injected such that when the separation and concentration structure is allowed to stand still, the liquid surface height of the density gradient solution is higher and preferably about 1 mm higher than the communication opening end of the upper tubular member 2 (reaching the tubular member 2 side). In other words, it is injected to an extent such that when the lower tubular member (tubular member 3) is separated, it is possible to perform a centrifugal operation so as to separate a component that has passed through the density gradient solution and moved to the side of the closed end 5 of the cylindrical member 3 into the tubular member 3 together with the majority of the density gradient solution, and a component of interest (cells) maintained on the density gradient solution into the tubular member 2 while the component is maintained in the tubular member 2. Then, an organism sample solution 26 is overlaid on the density gradient solution 25 a biological sample solution 26, the opening is sealed with a cap 4 (FIG. 5), and a centrifugal operation is carried out. Usually, centrifugation may be carried out at a low speed of from about 1000 to 2000×g. However, considering the density of cells of interest or the density of the density gradient solution, a condition that allows the cells of interest to be maintained on the density gradient solution is selected. For example, as long as cells of interest (target cells) are living tumor cells and centrifugation is performed in the manner described above, the density of the density gradient solution can be set in a range of 1.060 to 1.095 g/mL depending on the type of tumor cells. From the viewpoint of increasing the recovery rate of target cells, the density of the density gradient solution is preferably not less than 1.075 g/mL, preferably not less than 1.080 g/mL, more preferably not less than 1.085 g/mL, and still more preferably not less than 1.090 g/mL. From the viewpoint of increasing the concentration rate of target cells, it is preferably not more than 1.100 g/mL, more preferably not more than 1.096 g/mL, and still more preferably not more than 1.093 g/mL. More specifically, the density of the density gradient solution is preferably from 1.082 to 1.091 g/mL. In addition, the physiological osmotic pressure can be set in a range of 200 to 450 mOsm/kg. From the viewpoint of decreasing the mixing rate of dead cells, it is preferably not less than 280 mOsm/kg and more preferably not less than 300 mOs/kg. From the viewpoint of increasing the recovery rate of target cells, it is preferably not less than 300 mOsm/kg, more preferably not less than 350 mOsm/kg, and still more preferably not less than 380 mOsm/kg. More specifically, osmotic pressure of the density gradient solution is more preferably from 300 to 400 mOsm/kg. It is possible to arbitrarily select pH of the solution within a range that does not cause cells to be damaged. For example, the pH can be adjusted in a range of 6.8 to 7.8.

Figure 6:
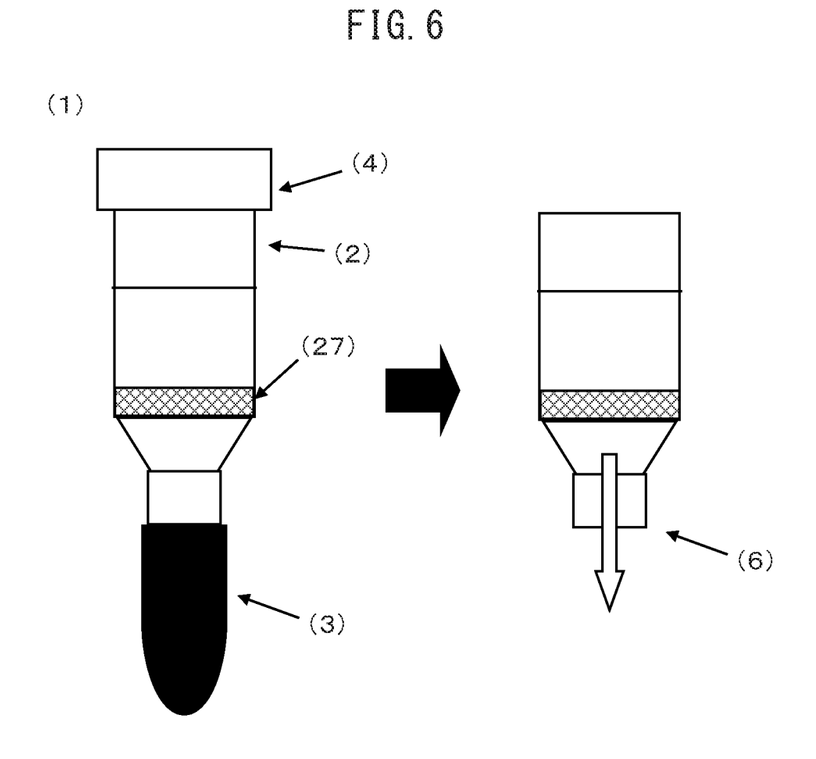
FIG. 6 is a view for explaining a method of concentrating target cells using the structure in FIG. 1.

As a result of the centrifugal separation operation, a component having a density greater than the density of the density gradient solution (such as dead cells) passes through the gradient layer of the density gradient solution and moves into the lower tubular member (tubular member 3). Meanwhile, cells 27 (target cells, for example, living tumor cells) of interest having a density smaller than the density of the density gradient solution are maintained on the density gradient solution in the upper tubular member (tubular member 2) (FIG. 6). Therefore, by separating the connected tubular members while maintaining the sealing of the opening to achieve the state illustrated in FIG. 1, it is possible to recover a fraction 27 containing the cells of interest (target cells) in the upper tubular member (tubular member 2) (FIG. 6). This fraction can be easily recovered without requiring a special skill by, for example, releasing the sealed state by removing the cap 4 to allow the fraction to drop downward. Meanwhile, the fraction which has moved to the lower tubular member (tubular member 3) can be discarded together with, for example, the tubular member.

The concentration step may further include a selection step for the purpose of concentrating target cells. In such a selection step, hemolysis treatment is performed when, for example, a blood sample is used. By conducting the hemolysis step, it is possible to reduce the cell number of erythrocytes, thereby selectively concentrating target cells. Such a selection step may be performed after or before centrifugation for concentration. After the selection step, centrifugation may be additionally performed.

After the hemolysis step, it is possible to conduct a detection step described later by recovering a pellet containing cells of interest via centrifugation of the hemolyzed solution. It is preferable to suspend the pellet in a solution containing a sugar such as mannitol, glucose, or sucrose because it is less likely to cause cells to be damaged. The solution containing a sugar may further contain electrolytes such as calcium and magnesium chloride, proteins such as BSA and casein, and proteins bound to hydrophilic polymers. The concentration of a sugar to be added may be adjusted to a concentration of an isotonic solution. When mannitol is used as a sugar, it may be adjusted as a final concentration to from 250 mM to 350 mM.

After the hemolysis step, desired cells that have been separated and recovered by centrifuging the hemolyzed solution can be detected by, for example, applying the cells to a slide, observing the cells with a microscope or an optical detector, or detecting the cells using a flow cytometry. When detecting cells by observation using a microscope or an optical detector, it is preferable to provide a suspension containing the cells to a spreading step.

Spreading Step

A spreading step is performed by spreading a concentrated liquid in the concentration step on a substrate. By spreading a concentrated liquid, it is possible to distribute cells contained in the concentrated liquid at intervals suitable for detection on a substrate. It is preferable to spread cells in a non-aggregated state. Preferably, the concentrated liquid is sufficiently suspended prior to spreading. Any technique can be used in the spreading step as long as cells can be distributed at intervals suitable for detection on a substrate. Although it is possible to simply apply a concentrated liquid on a substrate, further treatment may be performed, if necessary. As an example, it is also possible to spread cells by giving vibration or dielectrophoresis force after applying the concentrated liquid to the substrate. To spread the cells uniformly, it is preferable that holding holes are opened on the substrate. Arrangement of about one cell in each holding hole facilitates detection of target cells in the subsequent detection step. The concentrated liquid may be diluted for counting the number of cells in the concentrate liquid and spreading the appropriate number of cells depending on the spreading density of desired cells. It is also possible to measure a concentrated liquid to be spread and then spreading the concentrated liquid.

Figure 2:
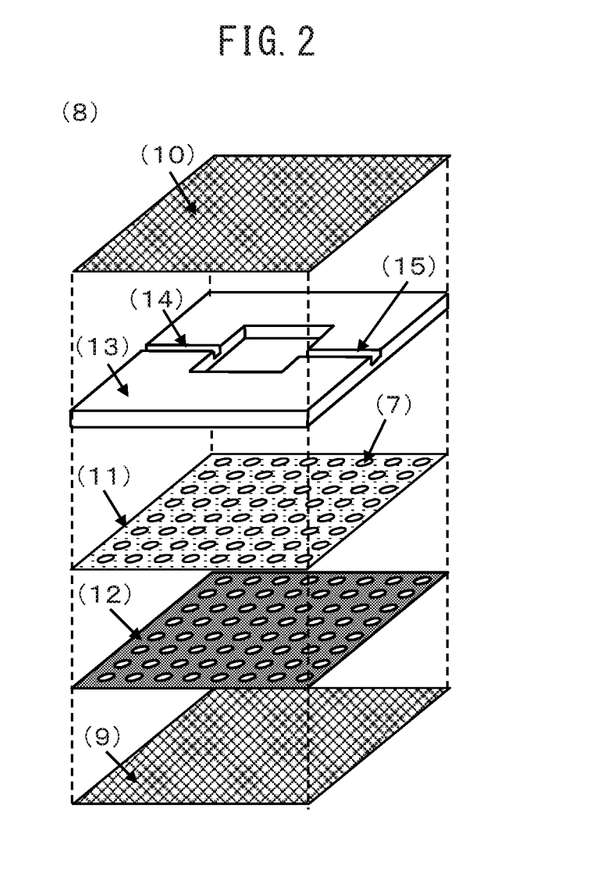
FIG. 2 is a view for explaining an organism sample detection structure used in the present invention.

As an instrument used in the spreading step, for example, an organism sample detection structure 8 in FIG. 2 can be used. This structure 8 is a structure having a plurality of holding holes (through holes) 7 holding cells for detecting light emitted by a substance indicating the presence of cells in the subsequent detection step, and the structure is disposed on a substrate 9. In addition, it is preferable that the substrate and an upper cover substrate 10 are made of a translucent material, and an electrode provided on the holding hole side and to the surface of the upper cover substrate of the substrate is a transparent electrode such as ITO. Accordingly, the light emitted from the holding holes can be observed from the upper or lower side of the substrate. Although the holding holes are formed on an insulator film 11, they may be provided with a light shielding film 12. By providing a light shielding film, for example, it is possible to reduce background noise due to autofluorescence of the insulating film itself or optical noise such as crosstalk noise caused by light leaked from adjacent holding holes, thereby exclusively detecting light emitted by an observation target substance inside of each holding hole with high sensitivity and high accuracy.

Further, the structure includes an accommodating unit 13 for accommodating a suspension containing the cells on the holding holes such that the holding holes are communicated with the accommodating unit. The accommodating unit also includes an inlet port 14 for introducing the cell suspension and a discharge port 15 for discharging the cell suspension.

Figure 3:
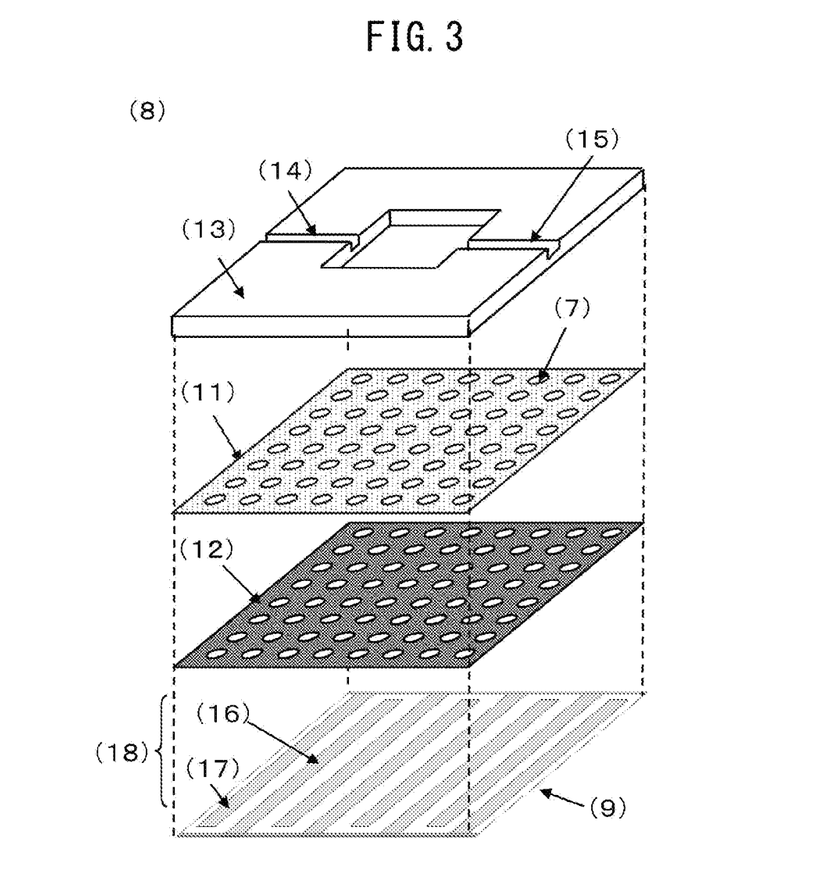
FIG. 3 is a view for explaining an organism sample detection structure used in the present invention.

As a method of capturing cells into holding holes utilizes dielectrophoresis force. Dielectrophoresis force allows a large number of holding holes to capture living cells in a very short time period of about several seconds. To cause dielectrophoresis force to act on the cells, an AC electric field can be applied to holding holes in a state where the accommodating unit and holding holes are filled with the suspension such that lines of electric force are localized in the portion of the holding holes. As a configuration for applying such an AC electric field, it is possible to employ a configuration illustrated in FIG. 3, in which electrodes 16 and 17 constituting a pair of electrodes (comb-shaped electrode 18) that are disposed at positions corresponding to different holding holes are provided to the surface on the holding hole side of the substrate, and the holding holes extend from the top surface to the comb-shaped electrode on the substrate, in addition to the structure of FIG. 2. In each configuration, the electrodes are exposed to the bottom of the holding holes and an AC voltage having a predetermined waveform is applied between the two electrodes, thereby making it possible to allow the holding holes to capture cells in the suspension by dielectrophoresis force. Further, when the holding holes are arranged in an array form, an electric field is generated by the voltage applied between the electrodes substantially equally in all of the holding holes, thereby directing cells towards all of the holding holes in the same manner so as to capture the cells.

Figure 4:
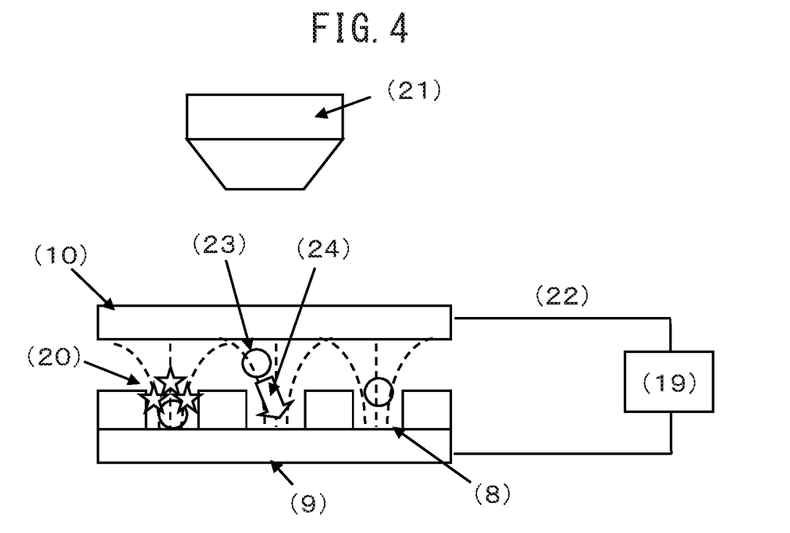
FIG. 4 is a view for explaining an organism sample detection structure and an organism sample detection device used in the present invention.

FIG. 4 is a view illustrating an organism sample detection device used in the present invention. In one example of an organism sample detection device used in the present invention, the device includes the substrate 9 and the upper cover substrate 10 illustrated in FIG. 2, an AC power source 19 for applying an AC voltage for generating a dielectrophoresis force 24 to the electrodes, and a detection unit 21 for detecting light 20 emitted by the substance indicating the presence of a cell 23 captured in a holding hole of the structure after the voltage is applied by the AC power source. As an example of the detection unit, a fluorescence microscope can be exemplified.

An AC power source is connected via a conductive wire 22 to the pair of electrodes of the structure. The AC power source is required to apply a voltage between the electrodes at a level sufficient for generating an electric field necessary for dielectrophoresis force for allowing cells to move into holding holes and capturing the cells. Specifically, it is possible to exemplify a power source that can apply an AC voltage, the peak of which is about 1V to 20V, and which has a waveform such as a sine wave, a square wave, a triangular wave, or a trapezoidal wave with a frequency of about 10 kHz to 10 MHz. It is particularly preferable to use, as a waveform having a frequency that allows living cells to move and each holding hole to capture only one cell and, a square wave having a frequency of 100 kHz to 3 MHz. The AC voltage of such a waveform instantly reaches a predetermined peak voltage as compared with a case in which the waveform is a square wave, a sine wave, a triangular wave, or a trapezoidal wave, which makes it possible to allow cells to move quickly towards holding holes so as to reduce a probability that two or more cells enter a holding hole to overlap each other (to increase a probability that only one cell can be captured in one holding hole). Although cells can be regarded as electrical capacitors, an electric current becomes unlikely to flow into cells captured in the holding holes, and thus, lines of electric force are hardly generated while the peak voltage of the square wave does not change. As a result, dielectrophoresis force is hardly generated in holding holes capturing cells. Therefore, once cells are captured in holding holes, a probability that another cell is captured in the same holding hole decreases, which, in turn, causes lines of electric force to be generated, thereby allowing cells to be captured sequentially in other holding holes in which dielectrophoresis force is generated (empty holding holes in which no cell is captured).

In an organism sample detection device used in the present invention, it is preferable to employ a power source for generating an AC voltage that does not have a DC component. This is because when an AC voltage having a DC component is applied, biased force derived from electrostatic force generated by a DC component (electrophoresis force) causes cells to move in a particular direction, which makes it difficult to capture the cells by dielectrophoresis force. Further, when an AC voltage having a DC component is applied, ions contained in the suspension containing the cells cause an electrical reaction on the electrode surface so as to generate heat, which causes thermal motion of the cells. This makes it impossible to control the movement by dielectrophoresis force and difficult to allow the cells to move into the holding holes so as to be captured. Note that the AC voltage having a DC component is a voltage other than a voltage having a frequency duty ratio of 50%, a voltage having an offset, a voltage having an extremely long period (e.g., 1 second or longer), or the like.

In addition, it is possible to detect living cells after applying a voltage at least once to an organism sample captured in holding holes. A method of applying a voltage is not particularly limited as long as a voltage can be applied to an organism sample. For example, applying a voltage between electrodes provided to a structure used in the present invention can be exemplified. As a voltage, a DC voltage or AC voltage or both DC and AC voltages may be applied simultaneously or alternately. Conditions such as the magnitude of voltage and voltage application time can be set as appropriate and are not particularly limited unless most of cells including cells with high survival activity die. For example, when a DC voltage is applied, it is applied at several to several tens of volts (V) and the voltage application time is several nanoseconds to several milliseconds in one example. The voltage application time for DC voltage is preferably 1 millisecond at most because, for example, when a voltage is applied at about 50V for several minutes, most of cells including cells with high survival activity die. For example, when the structure of the present invention is used, the voltage is applied at 50 V for 30 microseconds in one example.

In addition, the AC voltage is not particularly limited as long as the voltage repeatedly becomes positive and negative in several nanoseconds to several hundred milliseconds. For example, it is possible to exemplify a power source that can apply an AC voltage, the peak of which is about 1V to 20V, and which has a waveform such as a sine wave, a square wave, a triangular wave, or a trapezoidal wave with a frequency of about 100 kHz to 3 MHz. The voltage application time for AC voltage is preferably not more than 30 minutes and more preferably not more than 15 minutes when the voltage is from about 1V to 20V.

The number of repetitions to apply the DC voltage or/and the AC voltage is not particularly limited as long as it is at least one time. However, when the voltage is repeatedly applied many times, most of cells including cells with high survival activity die. For example, when the structure of FIG. 2 is used, the number of repetitions to apply a DC voltage at 50V for 30 microseconds or the number of repetitions to apply a 1-MHz AC voltage at 20V can be exemplified as about 3 times.

By applying such a voltage (DC voltage and/or AC voltage), it is possible to kill cells having weak survival activity while their cell membranes are being damaged and select living cells having higher survival activity. In addition, as the power source for applying a voltage to the organism sample, an AC power source for inducing dielectrophoresis may be used.

Detection Step

In this step, target cells can be detected from cells that have been separated and recovered by centrifuging a hemolysis solution by utilizing a protein that is hardly expressed in the target cells. Examples of the protein that is hardly expressed in target cells include proteins regarding epithelial markers which are specifically expressed in epithelial cells and proteins regarding leukocyte markers which are specifically expressed in leukocytes. More specifically, cytokeratin (CK) and EpCAM (Epithelial cell adhesion molecule) can be exemplified as epithelial markers, and CD45 can be exemplified as a leukocyte marker. Twenty types of proteins such as CK1 to CK20 are known as CK, and any of them is included in proteins that are expressed in epithelial cells, which are available in the present invention.

In the detection step of the present invention, by detecting leukocyte markers, epithelial markers, or cells that do not express the combination thereof, it is possible to detect target cells. Further, cells having cell nucleus can be detected as target cells.

It is also possible to detect desired cells by size. It is known that many cancer cells have sizes greater than those of erythrocytes and leukocytes (Non Patent Literature: Rostagno P. et al., Anticancer Res., 17 (4A), 2481-2485 (1997)). It is therefore possible to accurately detect mesenchymal cells from tumor tissues that have experienced epithelial-mesenchymal transition by extracting cells having sizes greater than those of erythrocytes and leukocytes as cancer cells. Erythrocytes are in the disc form and have a diameter of about 7 to 8 μm and a thickness of about 2 μm in terms of size. Leukocytes are in the spherical form and have a diameter of about 6 to 15 μm in terms of size which may differ depending on type. Meanwhile, since cancer cells, and in particular CTC, have a size of about 10 to 30 μm, they can be detected as target cells having a size of preferably not less than 10 μm and more preferably not less than 15 μm.

Figure 7:
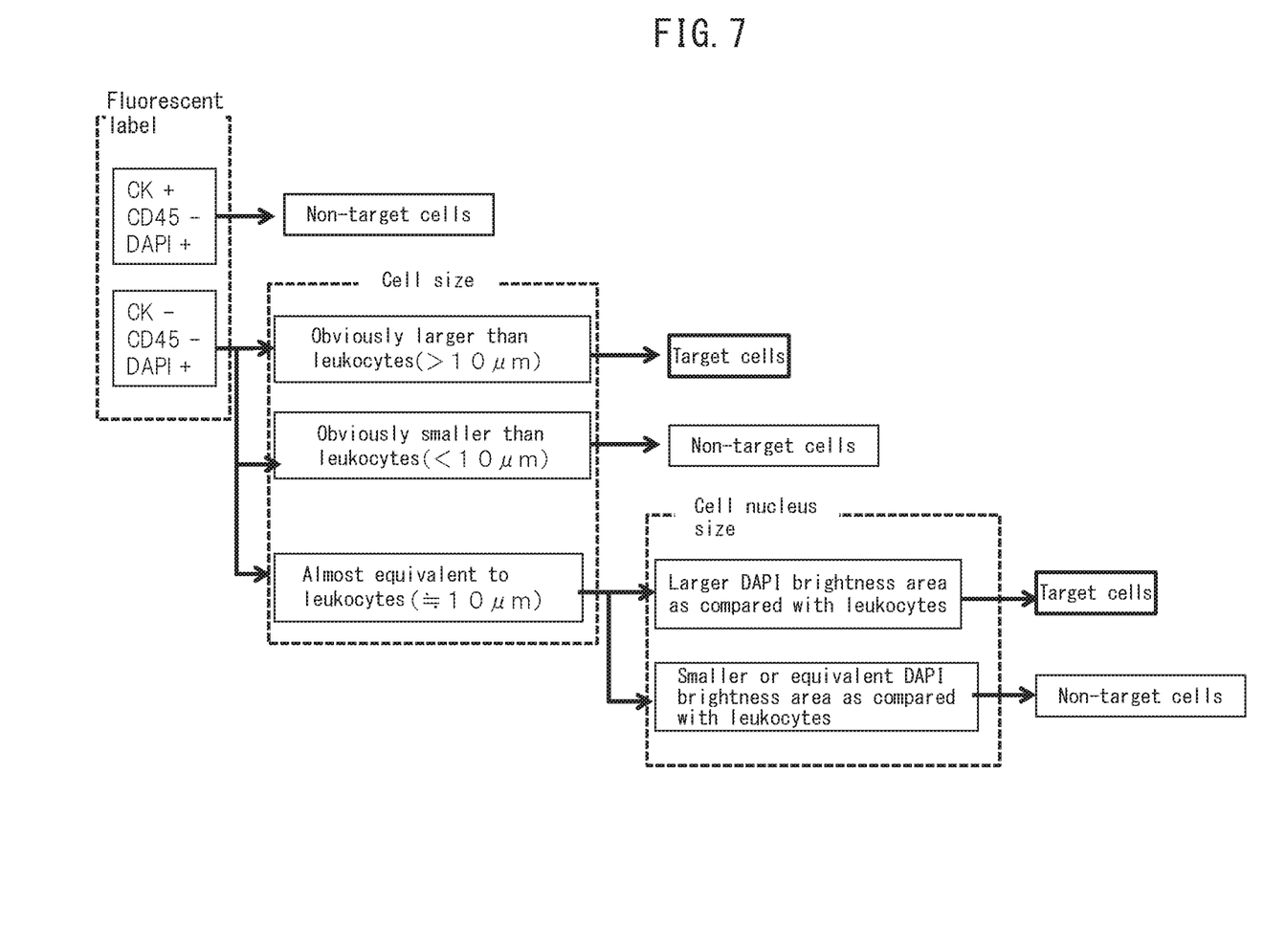
FIG. 7 is a view for explaining a flowchart for detecting target cells used in the present invention.

When the size of desired cells is substantially equivalent to the size of leukocytes, the desired cells may be further detected by the size of cell nucleus. It is known that many cancer cells have cell nucleus sizes greater than those of leukocytes. It is therefore possible to accurately detect desired cells having cell sizes substantially comparable to those of leukocytes by extracting cells having sizes greater than those of leukocytes as cancer cells. It is also possible to compare labeled regions in terms of the cell nucleus size using a reagent or the like which can label the cell nucleus region. In addition, for comparison of cell nucleus sizes, it is possible to detect, as target cells, cells having cell nucleus sizes greater than those of leukocytes with reference to cells found to be leukocytes (DAPI positive/CD45 positive/CK negative). An example of a flowchart for detecting target cells used in this step is illustrated in FIG. 7.

There is no particular limitation to a method of detecting expression of a protein in cells. The protein may be detected by staining the protein directly with a coloring reagent or a fluorescent reagent, by using a labeled antibody for the protein or a primary antibody against the protein and a labeled secondary antibody against the primary antibody, or by specifically amplifying the gene of the protein. In particular, the method of detection using a labeled antibody against the protein is a method, whereby the protein can be simply and specifically detected with high sensitivity, and therefore, it can be a preferred method. There is also no limitation to a substance for labeling the antibody. One example is a fluorescent substance such as fluorescein isothiocyanate (FITC), for example, Alexa Fluor (trade name). In the detection step, detected target cells can be counted. It is possible to perform counting manually or using software for automatically counting target cells based on an image obtained in the detection step.

Association Step

The survival prognosis of a patient can be determined in accordance with an identification table, graphs, and the like indicating the relationship between prognosis of the patient and the number of target cells in the patient based on the number of target cells detected in the detection step. Such an identification table and graphs can be determined by examining the number of target cells in patient groups in advance and further conducting follow-up examination of prognosis. In one example, prognosis determined by the present invention can be classified into a cured group, a relapse group, a group in need of treatment groups, and other groups. Further, the prognosis can also be classified based on survival rates such as the 1-year survival rate, 3-year survival rate, 5-year survival rate, and 10-year survival rate. This association step may be conducted by, for example, a medical assistant other than a physician. In addition, association can be automatically carried out using a device and software. Accordingly, the method of determining prognosis of the present invention can also be referred to as a preliminary method for diagnosis.

The relationship between the number of target cells and the prognosis of the patient can be determined by performing a follow-up study. Such relationship can be determined depending on the type and stage of a cancer disease from which the patient is suffering. Prognosis can be determined by predetermining the relationship between the number of target cells and the 1-year survival rate, 3-year survival rate, 5-year survival rate, or 10-year survival rate depending on the number of target cells per a given amount of the patient's blood after treatment.

Determination of prognosis according to the present invention enables provision of information with high accuracy for determination of therapeutic strategy or monitoring of therapeutic effects. Determination of prognosis according to the invention provides a physician with information on the risk of pathological state of the patient and the probability of survival, thereby allowing the physician to select the optimal therapy, which leads to reduction of the risk of performing unnecessary treatment on the patient. Therefore, it is possible to not only save the cost of unnecessary treatment but also contribute to the improvement of prognosis of the patient by optimal treatment selection. In addition, it is possible to employ the method of the present invention not only for prognostic diagnosis for cancer patients but also for early detection and metastasis diagnosis of tumors, as well as, for cancer diagnosis screening for healthy subjects other than cancer patients. According to the method of determining prognosis of the present invention, it is possible to further perform appropriate medical practice such as administration of anticancer agents, radiation therapy, and surgery on patients in a group in need of treatment and patients determined to have low survival rates.

As an example of the method of predicting prognosis of a cancer patient of the present invention, a method of detecting target cells contained in a blood sample is explained below. However, the present invention is not limited to the contents of the following description.

(1) Blood is collected from a patient suspected to have cancer or a cancer patient. Note that when collecting blood, it is possible to add an anticoagulant such as citrate, heparin, or ethylenediamine tetraacetic acid (EDTA). If necessary, the collected blood may be diluted with physiological saline or the like.

(2) A fraction containing target cells is separated by treating a predetermined amount of collected blood (or diluted blood) using density gradient centrifugation. Density gradient centrifugation is a method of separating cells based on specific gravity thereof. After the collected blood (or diluted blood) is overlaid on a medium forming a density gradient (density gradient solution), centrifugation is performed to collect a layer containing the target cells (upper layer), thereby obtaining a fraction containing the target cells from which unnecessary cells and waste have been removed. Note that before performing density gradient centrifugation, it is also possible to add a binder that can be bound to erythrocytes and leukocytes which are unnecessary cells (for example, RosetteSep (manufactured by StemCell Technologies)) to the collected blood (or diluted blood). The binder binds to erythrocytes, leukocytes, and/or surface antigens of these cells to form a cell aggregate, thereby allowing the density of the cells to increase. This facilitates separation of target cells by the density gradient centrifugation method.

(3) A solution containing ammonium chloride is added to a fraction containing the target cells obtained in (2) and the solution is stirred to hemolyze erythrocytes mixed in the fraction. This operation improves the observation of separated and recovered target cells.

(4) The hemolyzed solution containing target cells obtained in (3) is centrifuged to remove blood components and form the cells into a pellet, and then, the cells are suspended using a suitable solution.

(5) A suspension containing the target cells prepared in (4) is centrifuged again so as to recover the pellet containing the cells. If necessary, it is possible to add a step of resuspending the recovered pellet in the solution again and performing centrifugation.

(6) The concentrated target cells obtained in (5) is spread on a substrate by using, for example, the device described in WO2011/149032, and the holding unit is allowed to hold the target cells, followed by preservation and membrane permeabilization treatment of the cells. Examples of preservation treatment agents include formaldehyde, formaldehyde donor compounds (compounds capable of releasing formaldehyde when hydrolyzed), and aldehydes such as glutaraldehyde, alcohols such as methanol and ethanol, and solutions containing heavy metals. Examples of cell membrane permeabilization treatment agents include alcohols such as methanol and ethanol and surfactants such as saponin.

(7) Blocking treatment is performed using a protein for the holding unit holding target cells after preservation and membrane permeabilization treatment in order to prevent a non-specific reaction caused by an antibody. Thereafter, a protein modified with a fluorescent group, which is expressed in leukocytes, an antibody against a protein that is expressed in epithelial cells, or a reagent for fluorescent staining of cell nucleus is added, washing is conducted, and then, a fluorescence image and a bright field image of cells is observed by a fluorescent microscope. An anti-CD45 antibody can be used as an antibody against a protein expressed in leukocytes. An anti-CK antibody, an anti-EpCAM antibody, or the like can be used as an antibody against a protein expressed in epithelial cells. 4',6-Diamidino-2-phenylindole (DAPI), Hoechst 33342 (trade name), or the like can be used as a reagent for fluorescent staining of cell nucleus.

(8) Target cells can be detected based on the fluorescence image and the bright field image observed above. Target cells are cells in which the cell nucleus is labeled, which are not labeled with neither an anti-CD45 antibody nor an anti-CK antibody, and which have shapes larger than those of erythrocytes and leukocytes in the bright-field image.

The present invention is explained in more detail with reference to the Examples and Comparative Examples described below. However, the present invention is not limited to these examples.

EXAMPLES

Example 1

Correlation of the Number of CK-Negative Cells and the Pathological State (1) Blood was collected four times from a gastric cancer patient whose informed consent was obtained. Blood was collected from the patient at timings as defined below:

a timing when organ metastasis is not observed while only lymph node metastasis is observed, which corresponds to stage IV, and chemotherapy is yet conducted (blood collection 1), a timing when 4 weeks have passed from blood collection 1, and no changes are observed in pathological state after the completion of two cycles of chemotherapy (blood collection 2), a timing when 4 weeks have passed from blood collection 2, and no changes are observed in pathological state based on CT image diagnosis (blood collection 3), or a timing when 7 weeks have passed from blood collection 3, and aggravation of pathological state, which causes obstruction of passage of food during meals, has been confirmed (blood collection 4).

The patient died within 6 months after blood collection 4.

(2) A diluted blood sample was prepared by adding physiological saline and a leukocyte-platelet binding agent (manufactured by RosetteSep, StemCell Technologies Inc.) to the blood collected in (1).

(3) The diluted blood sample prepared above was overlaid on a density gradient solution having a density of 1.091 g/mL and centrifuged at 2000×g for 10 minutes at room temperature, and then, the supernatant was recovered.

(4) A hemolysate containing 0.9% ammonium chloride and 0.1% (w/v) potassium hydrogen carbonate was added to the supernatant obtained in (3) to result in 30 mL, followed by centrifugation at 300×g for 10 minutes at room temperature. This operation causes erythrocytes mixed in the supernatant to be destroyed, thereby facilitating observation of separated and recovered cells.

(5) After removing the supernatant, the pellet containing the separated and collected cells was resuspended in 30 mL of a solution containing 300 mM mannitol, the solution was centrifuged at 300×g for 5 minutes at room temperature, and the supernatant was removed. The resultant was resuspended in 30 mL of a solution containing 300 mM mannitol, the suspension was centrifuged at 300×g for 5 minutes at room temperature, and the supernatant was removed. This operation is intended to remove the blood components and concentrate target cells.

(6) The suspension containing cells from which the supernatant was removed in (5) was spread over a cell diagnostic chip and an AC voltage was applied thereto for 3 minutes, thereby allowing a holding unit included in the chip to hold the cells. The cell diagnostic chip used in the Examples has a structure in which an insulator having a plurality of micropores with a diameter of 30 μm and a depth of 40 μm and a holding unit formed with a light-shielding chromium film, which is placed between the insulator and the lower electrode substrate, are sandwiched between a spacer with a thickness of 1 mm and the lower electrode substrate, and the spacer is sandwiched between the upper electrode substrate and the lower electrode substrate.

(7) A 300 mM mannitol aqueous solution containing 0.01% (w/v) poly-L-lysine was introduced while an AC voltage was applied under the condition in (6) for 3 minutes, application of the AC voltage was terminated, and the aqueous solution was removed by suction.

(8) An aqueous solution containing 50% (v/v) ethanol and 1% (w/v) formaldehyde (hereinafter referred to as "cell-membrane-permeable reagent") was introduced and allowed to stand still for 10 minutes, and thus, the cells introduced into the holding unit were allowed to permeate through the cell membrane and sampled.

(9) The cell-membrane-permeable reagent was removed by suction and PBS (Phosphate buffered saline) was introduced, thereby washing the remaining cell-membrane-permeable reagent.

(10) An aqueous solution containing a fluorescent-labeled antibody capable of specifically binding to a protein inside and outside of a cell membrane and a fluorescent reagent for labeling cell nucleus (DAPI:4',6-diamidino-2-phenylindole (Dojindo Laboratories)) (hereinafter referred to as "labeling reagent") was introduced and allowed to stand still for 30 minutes. Note that an antibody against CD45 expressed on the leukocyte surface (Beckman-Coulter) and an antibody against CK expressed in cytoplasm of epithelial cells (Miltenyi Biotec) were used as the labelled antibody.

(11) A labeling reagent was removed by suction and PBS was introduced, thereby removing the remaining labeling reagent.

(12) After the cell diagnostic chip containing cells labelled in were placed on a stage of a fluorescence microscope, an image of the holding unit as a whole was taken to observe all cells captured in a plurality of holding holes. For this purpose, a fluorescence microscope (IX71; Olympus) equipped with a computer controlled electric stage and an electron multiplying cooled CCD camera (EMCCD; FLOVEL, ADT-100) was used. LabVIEW (National Instruments) was used for image acquisition and analysis software.

(13) Among cells image-captured in (12), cells, which are stained with DAPI indicating the presence of cell nucleus (DAPI-positive), which are not stained with an antibody against CD45 expressed in leukocytes (CD45-negative), which are not stained with an antibody against CK indicating the acquisition of epithelial characteristics (CK-negative), and which have cell shapes larger than those of erythrocytes or leukocytes in the bright-field image, were counted as target cells satisfying the above features (DAPI-positive/CD45-negative/CK-negative cells).

Comparative Example 1

Detection of
DAPI-Positive/CD45-Negative/CK-Positive Cells
(Part 1)

DAPI-positive/CD45-negative/CK-positive cells were counted in the same manner as in Example 1 except that among the cells image-captured in (13) in Example 1, DAPI-positive/CD45-negative/CK-positive cells, which are DAPI positive, CD45 negative, and CK positive, were counted.

Comparative Example 2

Detection by CellSearch Method (Part 1)

Cells expressing EpCAM serving as an epithelial cell marker were concentrated using blood collected by blood collection in (1) in Example 1. CTC counting was conducted using the CellSearch system (Janssen Diagnostics), which is a prior art technology capable of measurement of DAPI-positive, CD45-negative, and CK-positive cells.

Table 1 lists the results of the number of detected cells in Example 1 and Comparative Examples 1 and 2. In the case of blood collection 4 where the pathological state deteriorated, the number of CK-negative cells in Example 1 was 23 cells/3 mL, which was greater than the number of cells counted in Comparative Example 1 (0 cells/3 mL of blood) and Comparative Example 2 (0 cells/3 mL of blood). The correlation with the pathological state was confirmed. Further, the temporal changes in the number of detected CK-negative cells in Example 1 tended to increase whereas the number of detected CK-positive cells decreased in Comparative Examples 1 and 2. This result is correlated with the patient's prognosis, suggesting that it is possible to predict prognosis with high accuracy. Further, there was no increase in the number of detected CK-negative cells in Example 1 while there was an increase in the number of detected CK-positive cells associated with breakdown of cancer tissue due to chemotherapy for blood collection 2 in Comparative Example 1. This result indicates that breakdown of tissue due to chemotherapy does not affect a sharp increase in the number of detected. CK-negative cells, and therefore, it is possible to avoid the risk of giving false information in predicting therapeutic effects.

TABLE 1

| | Number of detected cells counted per 3 mL of blood | | | |
|---|---|---|---|---|
| | Blood collection 1 | Blood collection 2 | Blood collection 3 | Blood collection 4 |
| Example 1 | 3 | 5 | 11 | 23 |
| Comparative Example 1 | 2 | 61 | 0 | 0 |
| Comparative Example 2 | 4 | 1 | 0 | 0 |

Comparative Example 3

Comparison Based on Blood Test Items

With the use of blood collected in (1) in Example 1, the values of CEA and CA19-9, which have been conventionally used as diagnostic markers for diagnosis of tumor digestive organs, were determined.

Table 2 lists the results in Comparative Example 3. All blood samples had CA19-9 values which are not more than the reference value (37 U/mL) indicating normal levels. There was no correlation with the pathological state. All blood samples had CEA values which are not less than the reference value (5 ng/mL) indicating normal levels. However, the values decreased over time from blood collection 1 to blood collection 3, which apparently indicated therapeutic effects. Meanwhile, there was a tendency in blood collection 4 that the pathological state deteriorated, and the CEA value increased. The result indicates that it is difficult to predict prognosis including therapeutic effects based on measurement of CEA.

TABLE 2

| | | Blood collection 1 | Blood collection 2 | Blood collection 3 | Blood collection 4 |
|---|---|---|---|---|---|
| Comparative Example 3 | CEA(ng/mL) | 350 | 193 | 109 | 150 |
| | CA19-9(U/mL) | 7.6 | Not measured | 10.5 | 11 |

Example 2

Correlation Between the Number of CK-Negative Cells and the Period of Pathological Progression (Part 1)

Blood was collected from the cancer patients in the same manner as in (1) in Example 1 after the informed consent was obtained from the patient. Blood was collected from the following cancer patients:

stage IV breast cancer patient A in a state in which the period until the sum of tumor sizes increased by not less than 20% and the absolute value of the sum increased by not less than 5 mm, or the development of a de novo lesion was confirmed (PD: progressive disease) was 133 days after evaluation of CTC detection following blood collection;

stage IV breast cancer patient B for whom the period until PD was 295 days after evaluation of CTC detection following blood collection;

terminal stage IV oral cancer patient A for whom the period until PD was 17 days after evaluation of CTC detection following blood collection;

terminal stage IV oral cancer patient B for whom the period until PD was 83 days after evaluation of CTC detection following blood collection;

stage IV small cell lung cancer patient A for whom the period until PD was 91 days after evaluation of CTC detection following blood collection;

stage IV small cell lung cancer patient B for whom the period until PD was 268 days after evaluation of CTC detection following blood collection;

stage IB non-small cell lung cancer patient A for whom the period until PD was 137 days after evaluation of CTC detection following blood collection; or stage IA non-small cell lung cancer patient B for whom PD was not confirmed within 250 days after evaluation of CTC detection following blood collection.

Next, the number of target cells (DAPI-positive/CD45-negative/CK-negative cells) was counted, the cells being DAPI positive, CD45 negative, and CK negative selected from among cells image-captured in the same manner as in (2) to (12) in Example 1.

Example 3

Correlation Between the Number of CK-Negative Cells and the Period of Pathological Progression (Part 2)

Target cells (DAPI positive/CD45 negative/CK negative cells) were counted, the cells satisfying the conditions of being DAPI positive, CD45 negative, and CK negative and having cell shapes larger than those of erythrocytes or leukocytes in an image captured using blood collected in Example 2.

Comparative Example 4

Detection of DAPI-Positive/CD45-Negative/CK-Positive Cells (Part 2)

The number of DAPI-positive/CD45-negative/CK-positive cells was counted the cells being DAPI positive, CD45 negative, and CK positive on the image captured using the blood collected in Example 2.

Comparative Example 5

Detection by CellSearch Method (Part 2)

CTC counting was conducted using the CellSearch system (Janssen Diagnostics) in the same manner as in Comparative Example 2 except that blood collected in Example 2 was used.

Table 3 lists the results of the number of detected cells in Examples 2 and 3 and Comparative Examples 4 and 5. The number of counted CK-negative cells for the breast cancer patient A having a short period until PD and poor prognosis was 1926 cells/3 mL of blood, which was larger than the number of counted CK-negative cells for the breast cancer patient B having a long period until PD and favorable prognosis, which was 209 cells/3 mL of blood. The correlation between the cell count and the period of pathological progression was confirmed for the breast cancer patients in Example 2. Similarly, the number of counted cells for the small cell lung cancer patient A having a short period until PD and poor prognosis was 2994 cells/3 mL of blood, which was larger than the number of counted cells for the small cell lung cancer patient B having a long period until PD and favorable prognosis, which was 204 cells/3 mL of blood. The correlation between the cell count and the period of pathological progression was confirmed for the small cell lung cancer patients in Example 2. In addition, the number of counted cells for the non-small cell lung cancer patient A having a short period until PD and poor prognosis was 460 cells/3 mL of blood, which was larger than the number of counted cells for the non-small cell lung cancer patient B having a long period until PD and favorable prognosis, which was 130 cells/3 mL of blood. The correlation between the cell count and the period of pathological progression was confirmed for the non-small cell lung cancer patients. Meanwhile, the number of counted cells for the oral cancer patient A having a short period until PD and poor prognosis was 679 cells/3 mL of blood, which was smaller than the number of counted cells for the oral cancer patient B having a long period until PD and favorable prognosis, which was 1316 cells/3 mL of blood. The correlation between the cell count and the period of pathological progression was not confirmed for the oral cancer patients. This result for the oral cancer patients suggests that since the period until PD was short for both the oral cancer patient A having poor prognosis and the oral cancer patient B having favorable prognosis, the correlation between the cell count and prognosis could not be obtained. The period until aggravation of the pathological state was shortened as the number of detected CK negative cells increased for cancer types other than the oral cancer. The correlation between the cell count and the period of pathological progression was confirmed.

The number of counted CK-negative cells for the breast cancer patient A having a short period until PD and poor prognosis was 22 cells/3 mL of blood, which was larger than the number of counted CK-negative cells for the breast cancer patient B having a long period until PD and favorable prognosis, which was 1 cell/3 mL of blood. The correlation between the cell count and the period of pathological progression was confirmed for the breast cancer patients in Example 3. Similarly, the number of counted cells for the oral cancer patient A having a short period until PD and poor prognosis was 44 cells/3 mL of blood, which was larger than the number of counted cells for the oral cancer patient B having a long period until PD and favorable prognosis, which was 1 cell/3 mL of blood. The correlation between the cell count and the period of pathological progression was confirmed for the oral cancer patients in Example 3. In addition, the number of counted cells for the small cell lung cancer patient A having a short period until PD and poor prognosis was 41 cells/3 mL of blood, which was larger than the number of counted cells for the small cell lung cancer patient B having a long period until PD and favorable prognosis, which was 2 cells/3 mL of blood. The correlation between the cell count and the period of pathological progression was confirmed for the small cell lung cancer patients. Further, the number of counted cells for the non-small cell lung cancer patient A having a short period until PD and poor prognosis was 12 cells/3 mL of blood, which was larger than the number of counted cells for the non-small cell lung cancer patient B having a long period until PD and favorable prognosis, which was 6 cells/3 mL of blood. The correlation between the cell count and the period of pathological progression was confirmed for the non-small cell lung cancer patients. The period until aggravation of the pathological state was shortened as the number of detected CK negative cells having large cell shapes increased for any cancer or tumor. The correlation between the cell count and the period of pathological progression was confirmed.

Meanwhile, regarding the number of CK-positive cells detected in Comparative Example 4, the number of counted cells for the oral cancer patient A having a short period until PD and poor prognosis was 26 cells/3 mL of blood, which was larger than the number of counted cells for the oral cancer patient B having a long period until PD and favorable prognosis, which was 0 cells/3 mL of blood, only for oral cancer. However, the number of detected cells was 0 cells/3 mL of blood for breast cancer, small cell lung cancer, and non-small cell lung cancer. The correlation between the cell count and the period of pathological progression was not confirmed.

In addition, regarding the number of detected cells in Comparative Example 5, the number of detected cells for the small cell lung cancer patient A having a short period until PD and poor prognosis was 4 cells/3 mL of blood, which was larger than the number of counted cells for the small cell lung cancer patient B having a long period until PD and favorable prognosis, which was 0 cells/3 mL of blood, only for small cell lung cancer. However, the number of detected cells was 0 cells/3 mL of blood for breast cancer, oral cancer, and non-small cell lung cancer. The correlation between the cell count and the period of pathological progression was not confirmed.

These results indicate that the number of CK-negative cells is correlated with the patient's prognosis regardless of cancer or tumor, suggesting that it is possible to predict prognosis with high accuracy.

TABLE 3

| Patient | Period until PD (*1) | Number of detected cells counted per 3 mL of blood | | | |
|---|---|---|---|---|---|
| | | Example 2 | Example 3 | Comparative Example 4 | Comparative Example 5 |
| Breast cancer A | 133 | 1926 | 22 | 0 | 0 |
| Breast cancer B | 295 | 209 | 1 | 0 | 0 |
| Oral cancer A | 17 | 679 | 44 | 26 | 0 |
| Oral cancer B | 83 | 1316 | 1 | 0 | 0 |
| Small cell lung cancer A | 91 | 2994 | 41 | 0 | 4 |
| Small cell lung cancer B | 268 | 204 | 2 | 0 | 0 |

TABLE 3-continued

| | | Number of detected cells counted per 3 mL of blood | | | |
|---|---|---|---|---|---|
| Patient | Period until PD (*1) | Example 2 | Example 3 | Comparative Example 4 | Comparative Example 5 |
| Non-small cell lung cancer A | 137 | 460 | 12 | 0 | 0 |
| Non-small cell lung cancer B | 250< (*2) | 130 | 6 | 0 | 0 |

(*1) Period until PD from detection and evaluation of CTC after blood collection
(*2) Period of 250 days during which PD was not confirmed from the time point of detection and evaluation of CTC after blood collection

REFERENCE SIGNS LIST

1: Separation and concentration structure
2: Tubular member (upper side)
3: Tubular member (lower side)
4: Cap
5: Bottom
6: Communication opening
7: Holding hole
8: Organism sample detection structure
9: Substrate
10: Upper cover substrate
11: Insulator film
12: Light shielding film
13: Accommodating unit
14: Inlet port
15: Discharge port
16, 17: Electrode
18: Comb-shaped electrode
19: AC power source
20: Light
21: Detection unit
22: Conductive wire
23: Cell
24: Dielectrophoresis force
25: Density gradient solution
26: Organism sample solution
27: Fraction containing target cells

The invention claimed is:

1. A method of predicting survival prognosis for a cancer diagnosis, comprising:
   1) obtaining a concentrated liquid by concentrating target cells from an organism sample obtained from a patient;
   2) optically detecting the target cells with flow cytometry or observing the target cells with a microscope or an optical detector and counting target cells contained in the concentrated liquid, the target cells each having cell nucleus and not substantially expressing a leukocyte marker and a CK epithelial marker;
   3) determining the number of target cells in the patient based on the number of target cells optically detected in 2), wherein the number of counted target cells is indicative of overall prognosis; and
   4) predicting the survival prognosis for the cancer diagnosis by correlating the number of target cells with survival data obtained from a patient's previous prognosis, wherein the survival data comprises a correlation between the number of detected target cells and time period until patient death, and
   wherein the cancer is breast cancer, gastric cancer, lung cancer, or oral cancer.

2. The method according to claim 1, wherein the leukocyte marker is CD45.

3. The method according to claim 1, wherein the target cells have diameters of not less than 10 µm.

4. The method according to claim 1, wherein the target cells are circulating tumor cells (CTCs).

5. The method according to claim 1, wherein the obtaining a concentrated liquid is a concentration method based on a specific gravity difference of a biological sample.

6. The method according to claim 1, wherein the pretreatment includes concentrating a biological sample using a structure in which one end is closed to form a bottom and the other end has an opening and which has a cap for sealing the opening, and wherein the structure is formed with at least two tubular members such that the structure is separable at a separation unit.

7. The method according to claim 5, wherein specific gravity of a density gradient solution used in the concentration method is in a range of 1.082 to 1.091 g/mL.

8. The method according to claim 7, wherein osmotic pressure of a density gradient solution used in the concentration method is in a range of 300 to 400 mOsm/kg.

9. The method according to claim 1, further comprising 5) treating the patient when the number of target cells is above a predetermined threshold.

10. The method according to claim 9, wherein the treating comprises administration of anticancer agents, radiation therapy, or surgery on the patient suffering from cancer.

11. The method according to claim 1, wherein the cancer is lung cancer.

12. The method according to claim 1, wherein the cancer is breast cancer.

13. The method according to claim 1, wherein the cancer is oral cancer.

14. The method according to claim 11, wherein the lung cancer is small cell lung cancer.

15. The method according to claim 11, wherein the lung cancer is non-small cell lung cancer.

16. The method according to claim 1, wherein the cancer is gastric cancer.

17. A method of predicting prognosis of a subject having cancer, comprising:
   1) obtaining a concentrated liquid by concentrating target cells from an organism sample obtained from the subject;
   2) optically detecting the target cells with flow cytometry or observing the target cells with a microscope or an optical detector and counting target cells contained in the concentrated liquid, the target cells each having a cell nucleus and not substantially expressing a leukocyte marker and a CK epithelial marker;
   3) determining the number of target cells in the subject based on the number of target cells optically detected in 2), wherein the number of counted target cells is indicative of prognosis; and
   4) predicting the prognosis by correlating the number of target cells with prognosis data obtained from cancer patients whose prognosis has previously determined, wherein the prognosis data comprises a correlation between the number of detected target cells and one or more prognosis indicators selected from a group consisting of time period until patient death, the period of pathological progression, cured, relapsed, partial response (PR), complete response (CR), progressive disease (PD), stable disease (SD), and cancer stage, and wherein the cancer is breast cancer, gastric cancer, lung cancer, or oral cancer.

\* \* \* \* \*